(12) United States Patent
Knowlton

(10) Patent No.: US 8,900,181 B2
(45) Date of Patent: Dec. 2, 2014

(54) SKIN TREATMENT AND DRUG DELIVERY DEVICE

(75) Inventor: Edward W. Knowlton, Zehpyr Cove, NV (US)

(73) Assignee: SRGI Holdings, LLC, Henderson, NV (US)

( * ) Notice: Subject to any disclaimer, the term of this patent is extended or adjusted under 35 U.S.C. 154(b) by 439 days.

(21) Appl. No.: 12/972,013

(22) Filed: Dec. 17, 2010

(65) Prior Publication Data

US 2011/0257588 A1 Oct. 20, 2011

Related U.S. Application Data

(60) Provisional application No. 61/288,141, filed on Dec. 18, 2009.

(51) Int. Cl.

| | | |
|---|---|---|
| *A61B 17/20* | (2006.01) | |
| *A61B 17/32* | (2006.01) | |
| *A61M 35/00* | (2006.01) | |
| *A61B 17/322* | (2006.01) | |
| *A61M 5/46* | (2006.01) | |
| *A61B 17/00* | (2006.01) | |

(52) U.S. Cl.
CPC ............ *A61M 35/003* (2013.01); *A61B 17/322* (2013.01); *A61M 5/46* (2013.01); *A61B 2017/00792* (2013.01); *A61B 2017/3225* (2013.01)
USPC ............................................ 604/46; 606/167

(58) Field of Classification Search
USPC ...................... 604/46–48; 606/167
See application file for complete search history.

(56) References Cited

U.S. PATENT DOCUMENTS

| | | | |
|---|---|---|---|
| 5,964,729 A | 10/1999 | Choi et al. | |
| 7,354,423 B2 * | 4/2008 | Zelickson et al. | ............ 604/289 |
| 2004/0175690 A1* | 9/2004 | Mishra et al. | .................. 435/1.1 |
| 2006/0051404 A1 | 3/2006 | Yeshurun et al. | |
| 2007/0073217 A1 | 3/2007 | James | |

FOREIGN PATENT DOCUMENTS

KR    1020080100795 A    11/2008

* cited by examiner

*Primary Examiner* — Aarti B Berdichevsky
*Assistant Examiner* — Bradley Osinski
(74) *Attorney, Agent, or Firm* — IPR Law Group, PC

(57) ABSTRACT

A new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

31 Claims, 10 Drawing Sheets

SKIN TREATMENT AND DRUG DELIVERY DEVICE

RELATED APPLICATIONS

This application claims priority to U.S. Provisional Patent Application No. 61/288,141 filed Dec. 18, 2009, and entitled "Razor/Razor Blade Toolbox of Disposable Plastic Surgical Instruments," by Edward W. Knowlton, and is hereby incorporated herein by reference.

BACKGROUND

The aging process is most visibly depicted by the development of dependent skin laxity. This life long process may become evident as early as the third decade of life and will progressively worsen over subsequent decades. Histological research has shown that dependant stretching or age related laxity of the skin is due in part to progressive dermal atrophy associated with a reduction of skin tensile strength. When combined with the downward force of gravity, age related dermal atrophy will result in the two dimensional expansion of the skin envelope. The clinical manifestation of this physical-histological process is redundant skin laxity. The most affected areas are the head and neck, upper arms, thighs, breasts, lower abdomen and knee regions. The most visible of all areas is the head and neck. In this region, prominent "turkey gobbler" laxity of neck and "jowls" of the lower face are due to an unaesthetic dependency of skin in these areas. The frequency and negative societal impact of this aesthetic deformity has prompted the development of the "Face Lift" surgical procedure. Other related plastic surgical procedures in different regions are the Abdominoplasty (Abdomen), the Mastopexy (Breasts), and the Brachioplasty (Upper Arms). Some of the inherent adverse features of these surgical procedures are post-operative pain, scarring and the risk of surgical complications. Even though the aesthetic enhancement of these procedures is an acceptable tradeoff to the significant surgical incisions required, permanent and extensive scarring is always an incumbent part of these procedures. For this reason, Plastic Surgeons design these procedures to hide the extensive scarring around anatomical borders such as the hairline (Facelift), the inframmary fold (Mastopexy) and the inguinal crease (Abdominoplasty). However, other skin laxity regions such as the Suprapatellar (upper-front) knee are not amendable to Plastic Surgical resections due to the poor tradeoff with a more visible surgical scar. Recently, electromagnetic medical devices that create a reverse thermal gradient (i.e., Thermage) have attempted with variable success to tighten skin without surgery. At this time, these electromagnetic devices are best deployed in patients with a moderate amount of skin laxity due to the limitations of electromagnetic devices and potential side effects of surgery.

The foregoing examples of the related art and limitations related therewith are intended to be illustrative and not exclusive. Other limitations of the related art will become apparent upon a reading of the specification and a study of the drawings.

DETAILED DESCRIPTION OF EMBODIMENTS

Figure 1A:
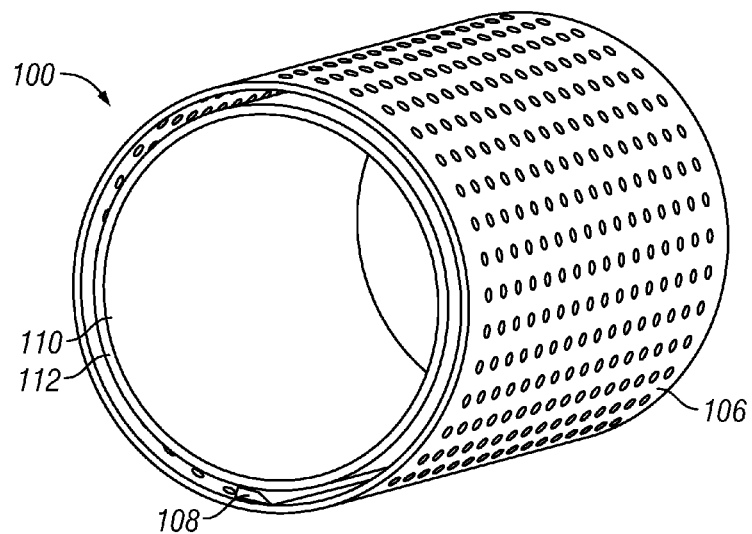
FIGS. 1(a)-(c) depict examples of a full rolling/rotating pixel drum/cylinder applicable to a skin surface for tightening.

The approach is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

A new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

For many patients who have age related skin laxity (for non-limiting examples, neck and face, arms, axillas, thighs, knees, buttocks, abdomen, bra line, ptosis of the breast), the minimally invasive surgical approach performs pixilated transection/resection of excess skin, replacing Plastic Surgery with its incumbent scarring. Typically, the procedure will be performed in an office setting under a local anesthetic with minimal perioperative discomfort. In comparison to a prolonged healing phase from plastic surgery, only a short recovery period will be required and the only recovery requirement will be the need to wear a support garment over the treatment area for 5 days. There will be little or no pain associated with the procedure. The small (½ mm to 1 mm) intradermal circular skin defects will be closed with the application of an adherent Flexan (3M) sheet. Functioning as a large butterfly bandage, the Flexan sheet can be pulled in a direction ("vector") that maximizes the aesthetic contouring of the treatment area. A compressive elastic garment will be applied over the dressing to further assist aesthetic contouring. After completion of the initial healing phase, the multiplicity of small linear scars within the treatment area will not be visibly apparent. It is also predicted that additional skin tightening will occur subsequently over several months due to the delayed wound healing response. Other potential applications include the treatment of Snoring/Sleep apnea, Orthopedics/Physiatry, Vaginal Tightening and tightening of gastrointestinal sphincters. During recovery, the treatment area is covered with a Flexan dressing and a compressive garment that promotes the wound healing process in the most effective direction.

Device for Skin Treatment

Figure 1B:
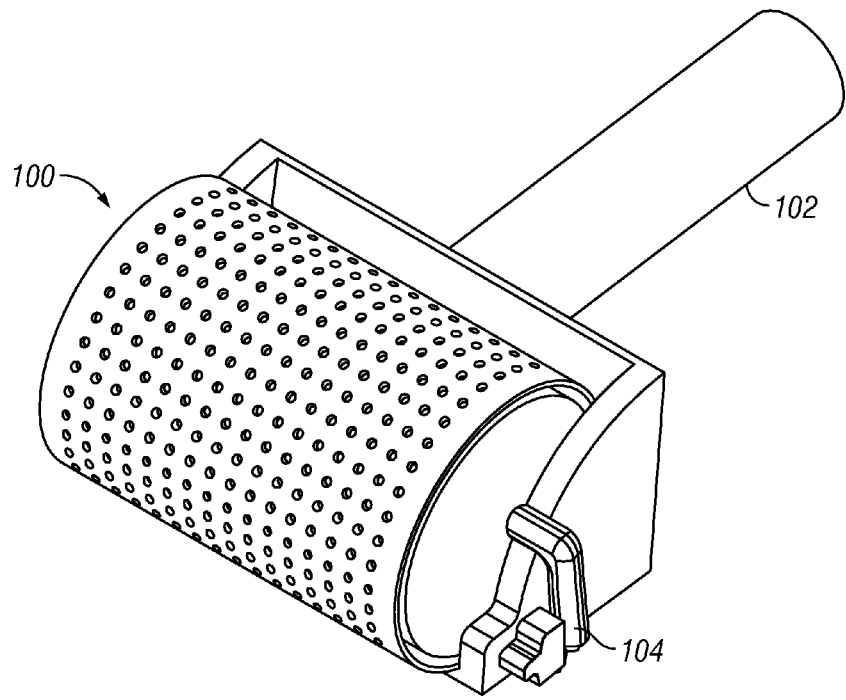
Figure 1C:
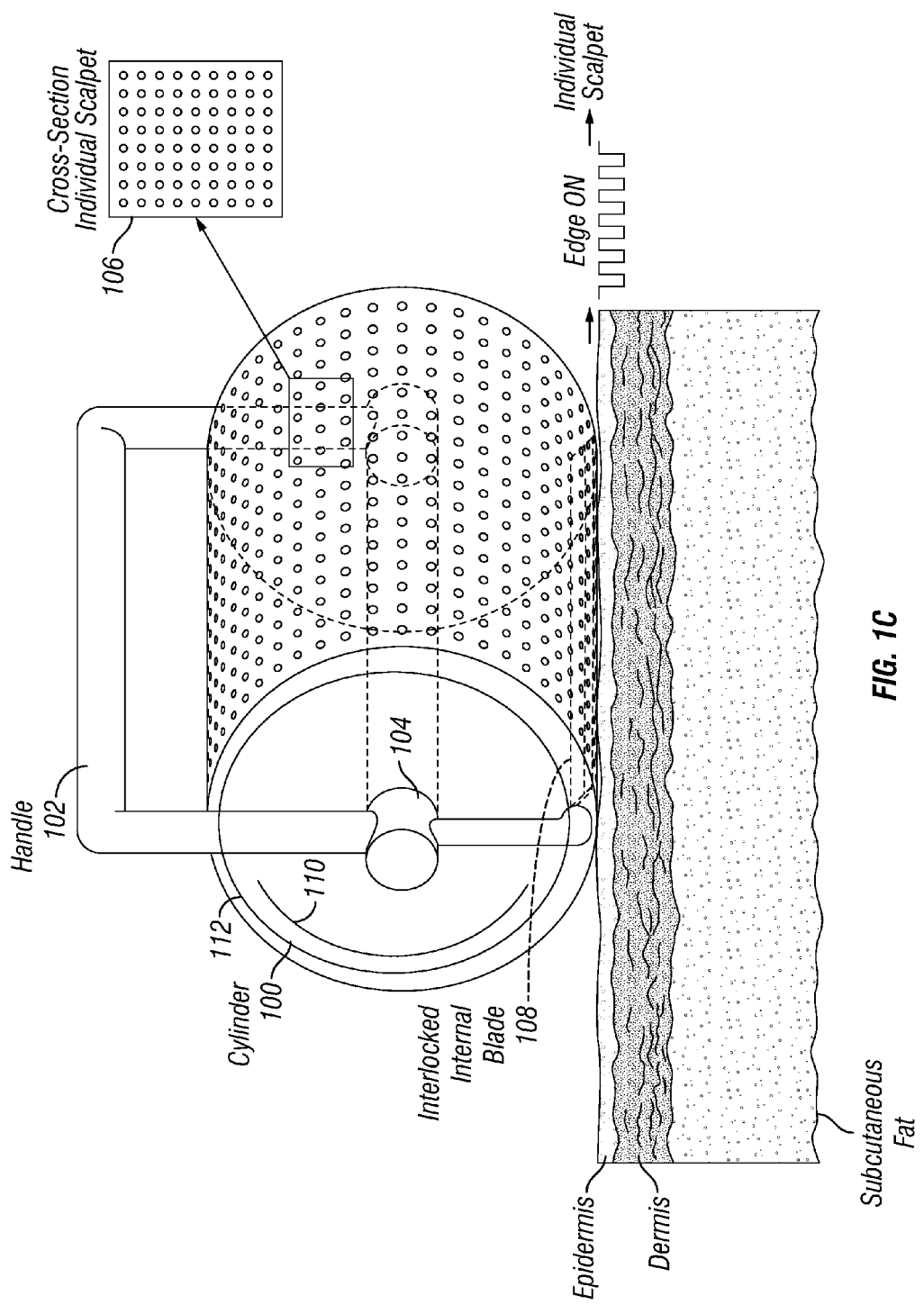

FIGS. 1(a)-(c) depict examples of a full rolling/rotating pixel drum/cylinder 100 applicable to the skin surface for tightening. Although the diagrams depict components as functionally separate, such depiction is merely for illustrative purposes. It will be apparent that the components portrayed in this figure can be arbitrarily combined or divided into separate hardware components.

Referring now to FIGS. 1(a)-(c), FIG. 1(a) depicts an example of rolling pixel drum 100, FIG. 1(b) depicts an example of a rolling pixel drum 100 assembled on a handle, and FIG. 1(c) depicts an example of a rolling pixel drum 100 being applied to the skin surface for tightening. FIGS. 2(a)-(d) further depict examples of dissected internal structure of a half drum depicted in FIGS. 1(a)-(d).

As with other pixel devices, the geometry of the pixel drum 100 can be a variety of shapes without limitation i.e., circular, semicircular, elliptical, square, flat, or rectangular. In some embodiments, the pixel drum 100 is supported by an axel/handle assembly 102 and rotated around a drum rotational component 104 powered by, e.g., an electric motor. In some embodiments, the pixel drum 100 can be placed on stand (not shown) when not in use, wherein the stand can also function as a battery recharger for the powered rotational component of the drum or the powered component of the syringe plunger. In some embodiments, a vacuum (not shown) can be applied to the skin surface of the pixel drum 100 and outriggers (not shown) can be deployed for tracking and stability of the pixel drum 100.

In some embodiments, the pixel drum 100 incorporates an array of scalpets 106 on the surface of the drum 100 to create small multiple (e.g., ½ mm to 1 mm) circular incisions referred to herein as skin plugs. In some embodiments, the border geometry of the scalpets can be designed to reduce pin cushioning ("trap door") while creating the skin plugs. The perimeter of each skin plug can also be lengthened by the scalpets to, for a non-limiting example, a, semicircular, elliptical, or square-shaped skin plug instead of a circular-shaped skin plug. In some embodiments, the length of the scalpets 106 may vary depending upon the thickness of the skin area selected by the surgeon for skin grafting purposes, i.e., partial thickness or full thickness.

When the drum 100 is applied to a skin surface, a blade 108 placed internal of the drum 100 transects the base of each skin plug created by the array of scalpets, wherein the internal blade 108 is connected to the central drum axel/handle assembly 102 and/or connected to outriggers attached to the central axel assembly 102. In some alternative embodiments, the internal blade 108 is not connected to the drum axel assembly 102 where the base of the incisions of skin is transected. In some embodiments, the internal blade 108 of the pixel drum 100 may oscillate either manually or be powered by an electric motor. Depending upon the density of the circular scalpets on the drum, a variable percentage of skin can be transected. It is predicted that up to 50% of the skin's surface area can be transected within an area of excessive skin laxity.

In some embodiments, an added pixel drum harvester 112 is placed inside the drum 100 to perform a skin grafting operation by harvesting and aligning the transected/pixilated skin incisions/plugs (pixel graft) from tissue of a pixel donor onto an adherent membrane 110 lined in the interior of the pixel drum 100. A narrow space is created between the array of scalpets 106 and the adherent membrane 110 for the internal blade 108.

In some embodiments, the blade 108 is placed external to the drum 100 and the scalpet array 106 where the base of the incised circular skin plugs is transected. In some embodiments, the external blade 108 is connected to the drum axel assembly 102 when the base of the incisions of skin is transected. In some alternative embodiments, the external blade 108 is not connected to the drum axel assembly 102 when the base of the incisions of skin is transected. The adherent membrane 110 that extracts and aligns the transected skin segments onto the membrane 110, which is later placed over a skin defect site of a patient. In some embodiments, blade 108 (either internal or external) can be a fenestrated layer of blade aligned to the scalpet array 106.

Figure 2A:
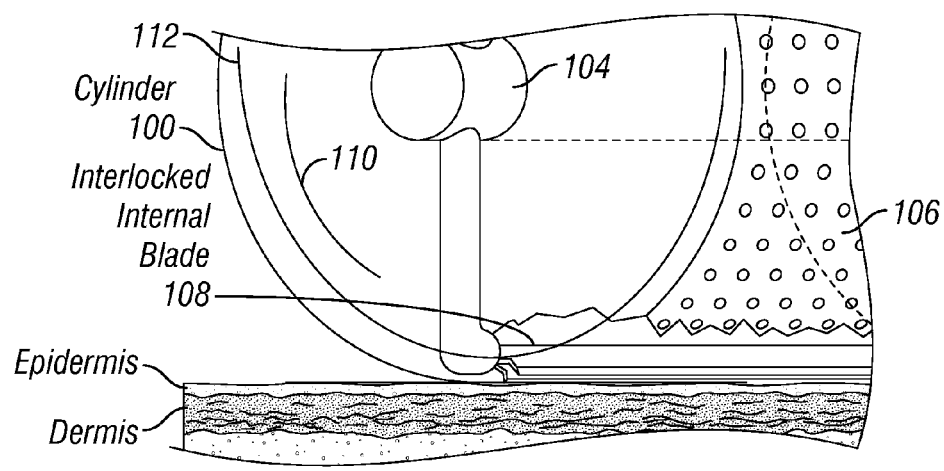
FIGS. 2(a)-(d) depict examples of dissected internal structure of a half drum depicted in FIGS. 1(a)-(d).
Figure 2B:
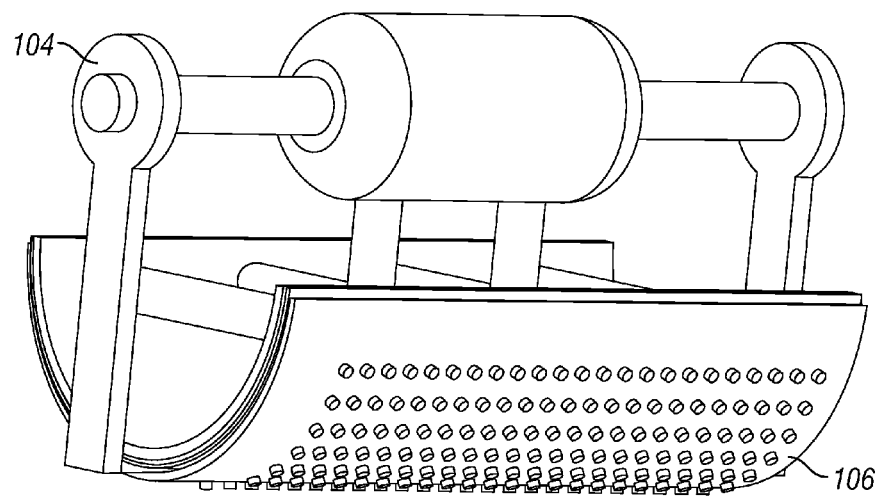
Figure 2C:
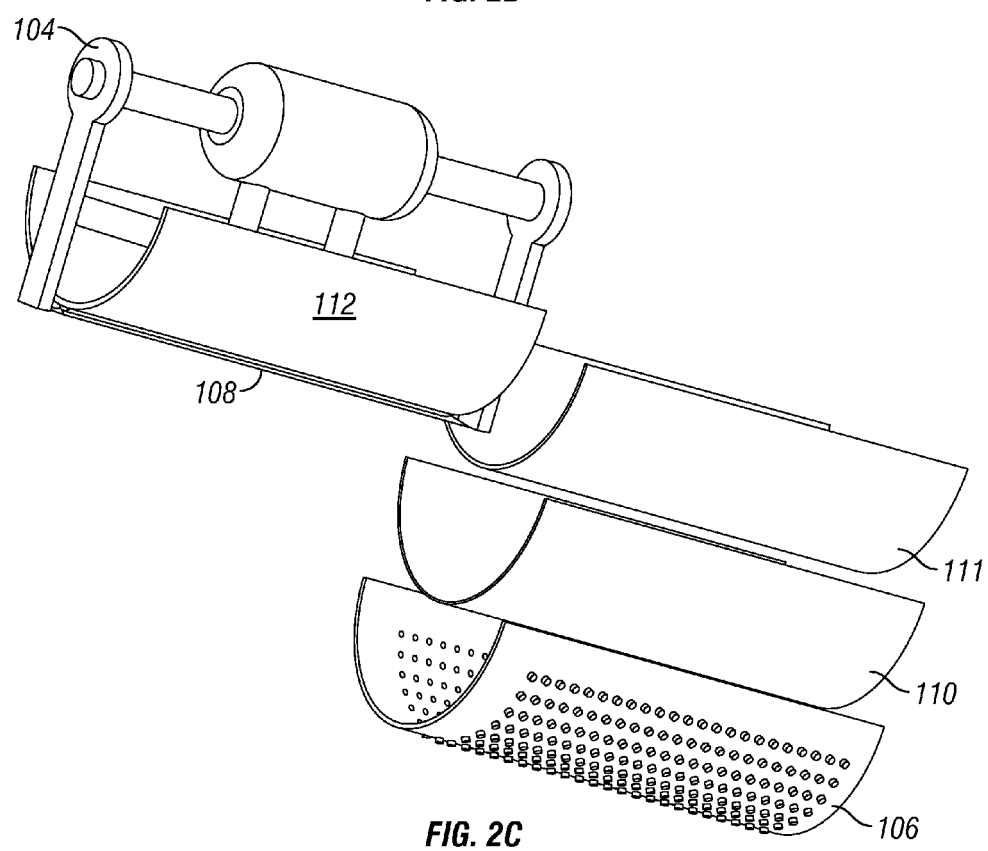
Figure 2D:
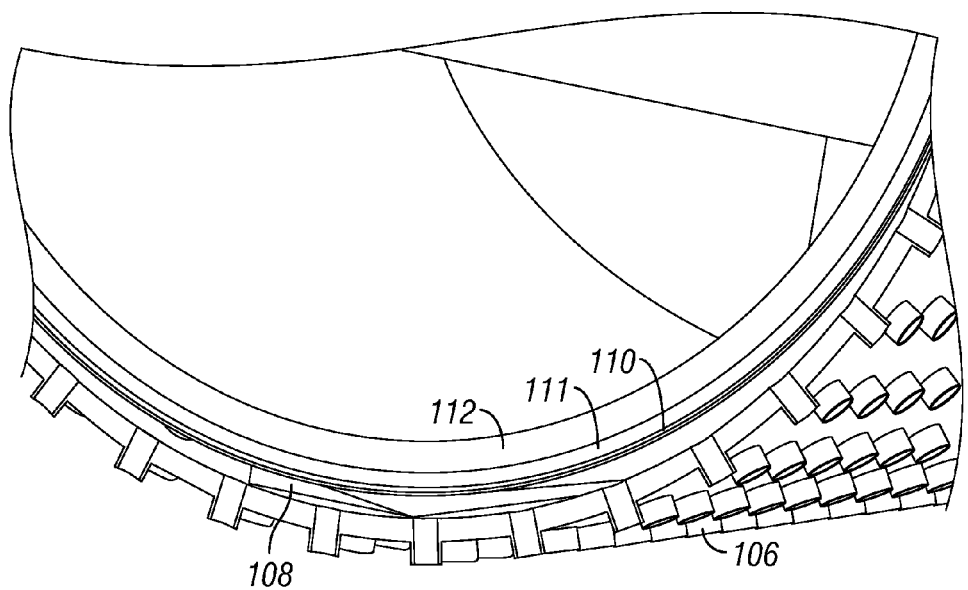

In some embodiments, the conformable adherent membrane 110 can be semi-porous to allow for drainage at a recipient skin defect when the membrane with the aligned transected skin segments is extracted from the drum and applied as a skin graft. In some embodiments, the adherent semi-porous drum membrane 110 can also have an elastic recoil property to bring the transected/pixilated skin plugs together for grafting onto the skin defect site of the recipient, i.e., the margins of each skin plug can be brought closer together as a more uniform sheet after the adherent membrane with pixilated grafts extracted from the drum 100. In some embodiments, the adherent semi-porous drum membrane 110 can also be expandable to cover a large surface area of the skin defect site of the recipient. In some embodiments, a sheet of adhesive backer 111 can be applied between the adherent membrane 110 and the drum harvester 112. The drum array of scalpets 106, blade 108, and adherent membrane 110 can be assembled together as a sleeve onto a preexisting drum 100 as shown in FIGS. 2(c)-(d).

In some embodiments, the internal drum harvester 112 of the pixel drum 110 is disposable and replaceable. Limit and/or control the use of the disposable components can be accomplished by means that includes but is not limited to electronic, eprom, mechanical, durability. The electronic and/or mechanical records and/or limits of number of drum rotations for the disposable drum as well as the time of use for the disposable drum can be recorded, controlled and/or limited either electronically or mechanically.

Figure 3A:
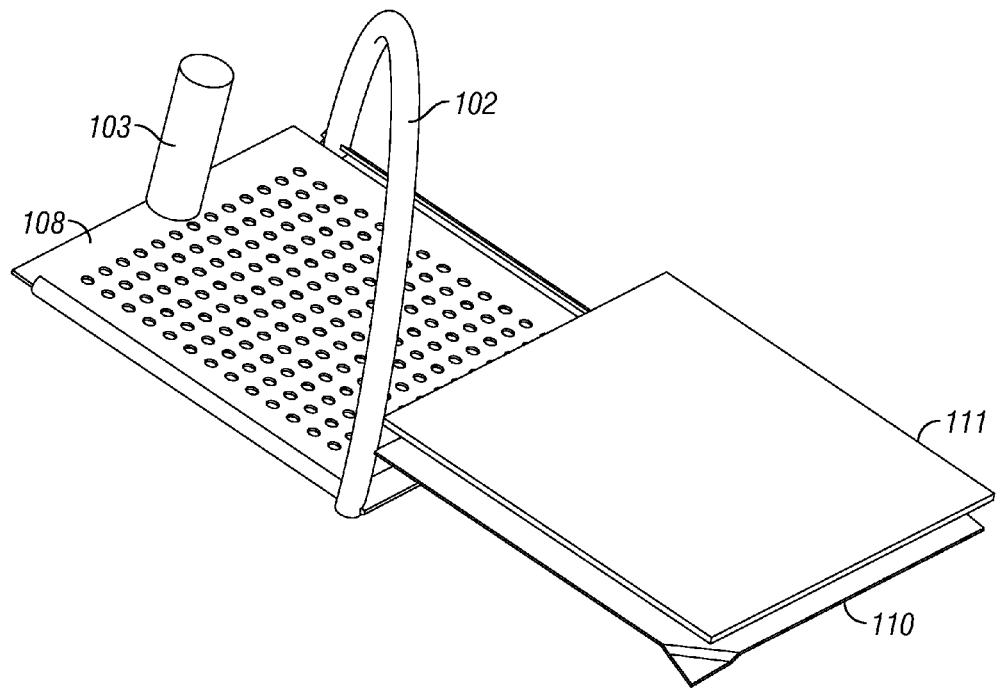
FIGS. 3(a)-(d) depict examples of an oscillating flat array of scalpets and blade either powered electrically or deployed manually (unpowered).
Figure 3B:
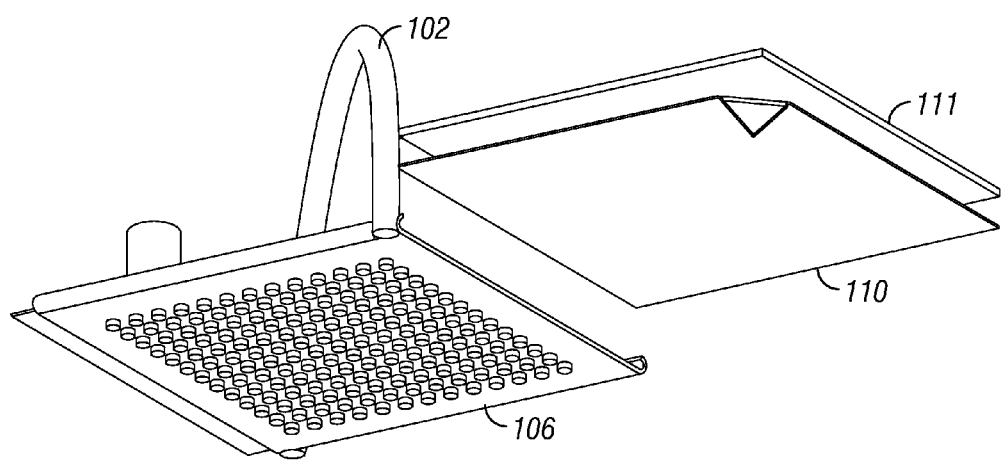
Figure 3C:
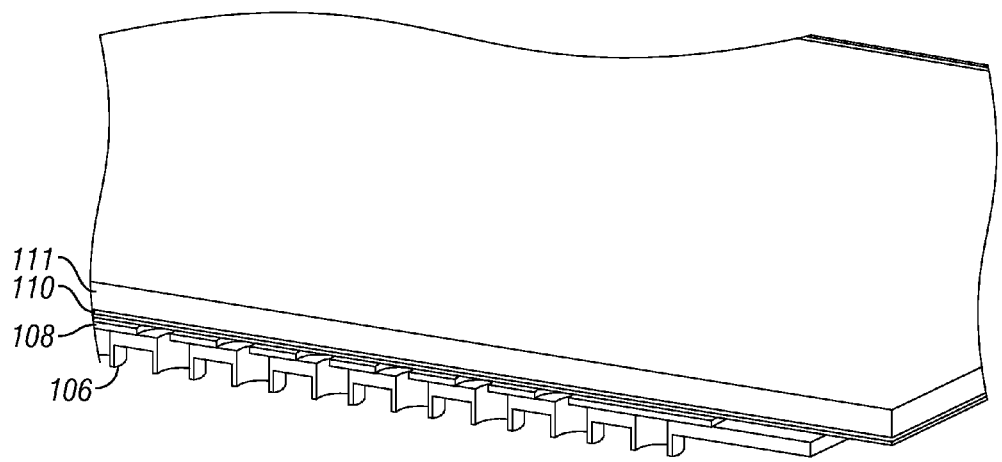
Figure 3D:
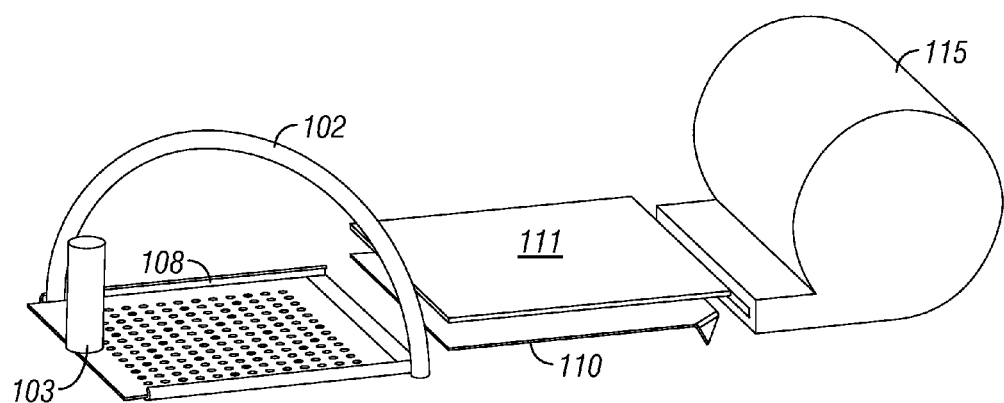

In some embodiments, an oscillating flat array of scalpets and blade as shown in FIGS. 3(a)-(d) either powered electrically or deployed manually (unpowered) can be used for skin tightening as alternative to the drum/cylinder depicted in FIGS. 1(a)-(c) and 2(a)-(d). Here, blade 108 can be a fenestrated layer of blade aligned to the scalpet array 106. FIGS. 3(a)-(b) depict top and bottom views of the flat array where the instrument handle 102 is separated from the blade handle 103 and the adherent membrane 110 can be peeled away from the adhesive backer 111. FIGS. 3(c) depict a close-up view of the flat array when the array of scalpets 106, blades 108, adherent membrane 110 and the adhesive backer 111 are assembled together. As assembled, the flat array of scalpets can be metered to provide a uniform harvest or a uniform resection. In some embodiments, the flat array of scalpets may further include a feeder component 115 for the adherent harvesting membrane 110 and adhesive backer 111 as shown in FIG. 3(d).

Figure 4:
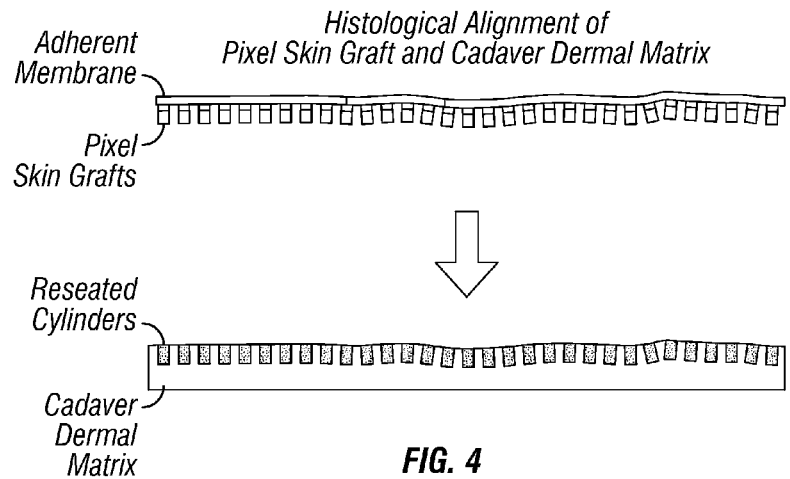
FIG. 4 depicts an example of a cadaver dermal matrix cylindrical transected similar in size to the harvested skin pixel grafts to provide histological alignment of the pixilated graft into the cadaver dermal framework.

In another skin grafting embodiment, the pixel graft is placed onto an irradiated cadaver dermal matrix (not shown). When cultured onto the dermal matrix, a graft of full thickness skin is created for the patient that is immunologically identical to the pixel donor. In some embodiments, the cadaver dermal matrix can also be cylindrical transected similar in size to the harvested skin pixel grafts to provide histological alignment of the pixilated graft into the cadaver dermal framework as shown in FIG. 4. In some embodiments, the percentage of harvest of the donor site can be determined in part by the induction of a normal dermal histology at the skin defect site of the recipient as shown in FIG. 4, i.e., a normal (smoother) surface topology of the skin graft is facilitated. With either the adherent membrane or the dermal matrix embodiment, major advantage of the pixel drum harvester includes the ability to harvest a large surface area for grafting with visible scarring of the patient's donor site significantly reduced or eliminated.

In some embodiments, the pixel drum 100 may evoke cellular and/or extracellular responses that are obligatory to the clinical outcomes achieved and a physical reduction of the skin surface area may occur due to the transected/pixilated skin, i.e., creation of the skin plugs. In addition, a subsequent tightening of the skin is predicted due to the delayed wound healing response. Each skin pixilation may initiate the obligate wound healing sequence in multiple phases:

The first phase of this sequence is the inflammatory phase in which degranulation of mast cells release histamine into the "wound". Histamine release may evoke dilatation of the capillary bed and increase vessel permeability into the extracellular space. This initial wound healing response occurs within the first day and will be evident as erythema on the skin's surface.

The second phase (of Fibroplasia) commences within 4-5 days of "wounding". During this phase, there is migration and mitotic multiplication of fibroblasts. Fibroplasia of the wound has two key features: the deposition of neocollagen and the myofibroblastic contraction of the wound. Histologically, the deposition of neocollagen can be identified microscopically as compaction and thickening of the dermis. Although this is a static process, the tensile strength of the wound significantly increases. The other feature of Fibroplasia is a dynamic physical process that results in a three dimensional contraction of the wound. This component feature of Fibroplasia is due to the active cellular contraction of myofibroblasts. Morphologically, myoblastic contraction of the wound will be visualized as a two dimensional tightening of the skin surface. Overall, the effect of Fibroplasia will be dermal contraction along with the deposition of a static supporting scaffolding of neocollagen with a tightened framework. The clinical effect can be seen as a delayed tightening of skin with smoothing of skin texture over several months. The clinical endpoint is a more youthful appearing skin envelope of the treatment area.

A third and final phase of the delayed wound healing response is maturation. During this phase there is a strengthening and remodeling of the treatment area due to an increased cross-linkage of the collagen fibril matrix (of the dermis). This final stage commences with 6 to 12 months after "wounding" and may extend for at least 1-2 years. Small pixilated resections of skin should preserve the normal dermal architecture during this delayed wound healing process without the creation of an evident scar that typically occurs with a larger surgical resection of skin. Lastly, there is a related stimulation and rejuvenation of the epidermis from the release of epidermal growth hormone. The delayed wound healing response can be evoked, with scar collagen deposition, within tissues (such as muscle or fat) with minimal pre-existing collagen matrix.

Other than tightening skin for aesthetic purposes, the pixel drum 100 described above may have additional medically related applications. In some embodiments, the pixel drum 100 can transect a variable portion of any soft tissue structure without resorting to a standard surgical resection. More specifically, the reduction of an actinic damaged area of skin via the pixel drum 100 should reduce the incidence of skin cancer. For the treatment of sleep apnea and snoring, a pixilated mucosal reduction (soft palate, base of the tongue and lateral pharyngeal walls) via the pixel drum 100 would reduce the significant morbidity associated with more standard surgical procedures. For birth injuries of the vaginal vault, pixilated skin and vaginal mucosal resection via the pixel drum 100 would reestablish normal pre-partum geometry and function without resorting to an A&P resection. Related female stress incontinence could also be corrected in a similar fashion.

Drug Delivery Device

For the most part, the parenteral delivery of drugs is still accomplished from an injection with a syringe and needle. To circumvent the negative features of the needle and syringe system, the topical absorption of medication transcutaneously through an occlusive patch was developed. However, both of these drug delivery systems have significant drawbacks. The human aversion to a needle injection has not abated during the nearly two centuries of its use. The variable systemic absorption of either a subcutaneous or intramuscular drug injection reduces drug efficacy and may increase the incidence of adverse patient responses. Depending upon the lipid or aqueous carrier fluid of the drug, the topically applied occlusive patch is plagued with variable absorption across an epidermal barrier. For patients who require local anesthesia over a large surface area of skin, neither the syringe/needle injections nor topical anesthetics are ideal. The syringe/needle "field" injections are often painful and may instill excessive amounts of the local anesthetic that may cause systemic toxicity. Topical anesthetics rarely provide the level of anesthesia required for skin related procedures.

Figure 5:
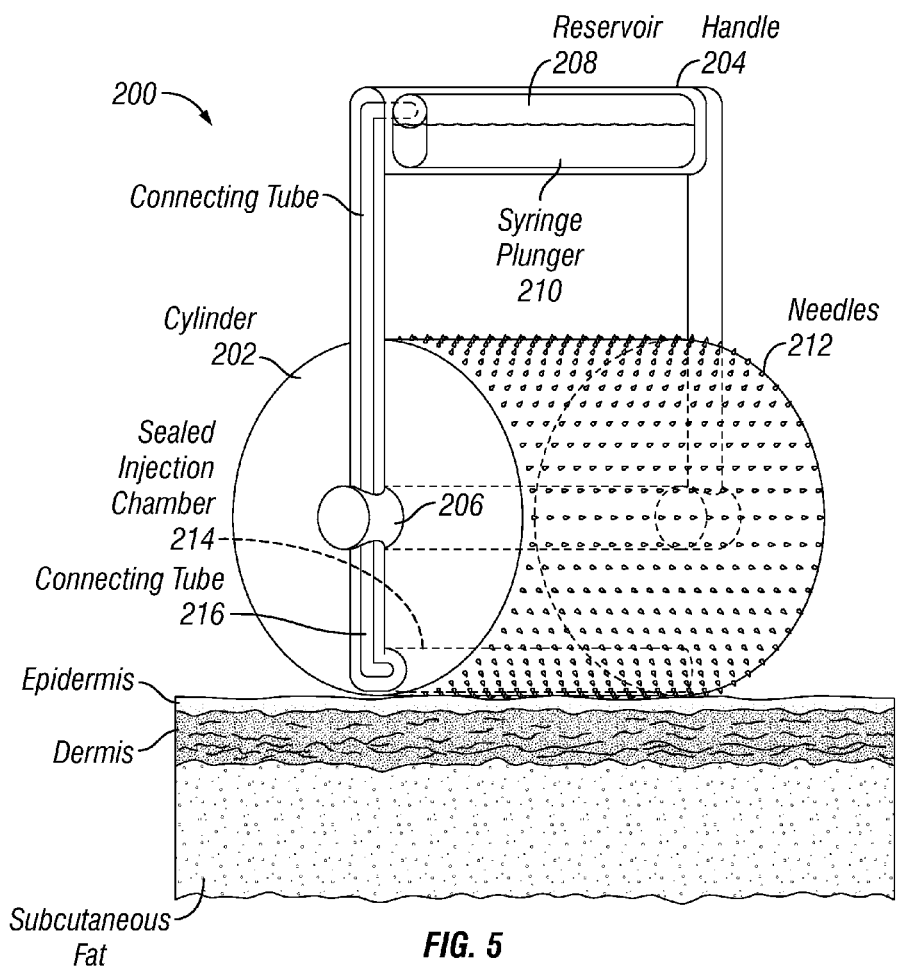
FIG. 5 depicts example of a drum-based drug delivery device being applied to the skin surface for drug injection.

The drug delivery device 200 depicted in FIG. 5 successfully addresses the limitations and drawbacks of other drug delivery systems. A drum/cylinder 202 depicted in FIG. 5 is supported by an axel/handle assembly 204 and rotated around a drum rotation component 206. The handle assembly 204 may further include a reservoir 208 of drugs to be delivered and a syringe plunger 210. The surface of the drum 202 is covered by an array of needles 212 of uniform length, which provide a uniform intradermal (or subdermal) injection depth with a more controlled volume of the drug injected into the skin of the patient. During operation, the syringe plunger 210 pushes the drug out of the reservoir 208 to be injected into a sealed injection chamber 214 inside the drum 202 via connecting tube 216. The drug is eventually delivered into the patient's skin at a uniform depth when the array of needles 212 is pushed into a patient's skin until the surface of the drum 202 hits the skin. Non-anesthetized skip area is avoided and a more uniform pattern of cutaneous anesthesia is created. The rolling drum application of the drug delivery device 200 also instills the local anesthetic faster with less discomfort to the patient.

Figure 6A:
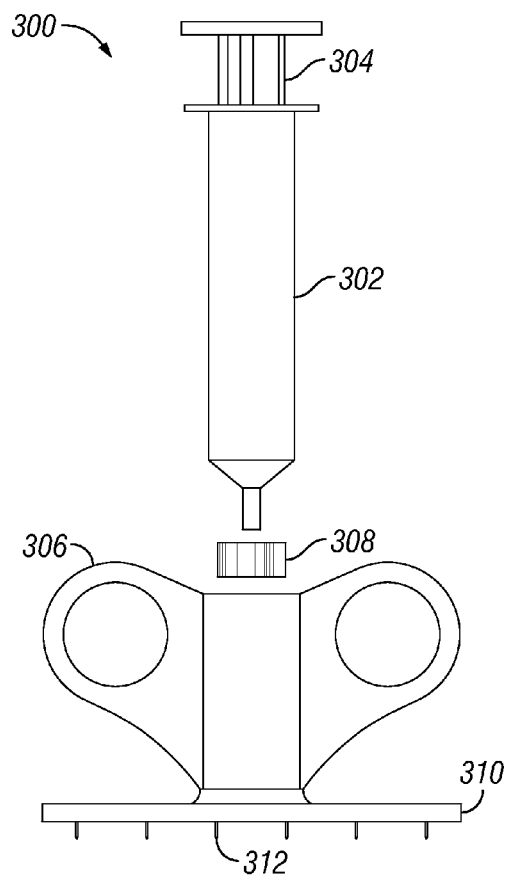
FIG. 6(a)-(c) depict examples of a drug delivery device based on flat array of needles being applied to the skin surface for drug injection.
Figure 6B:
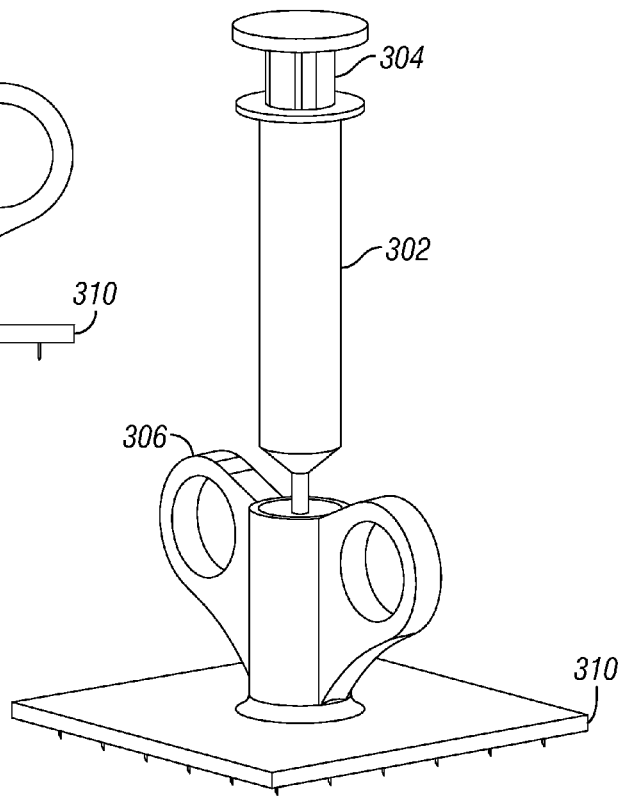
Figure 6C:
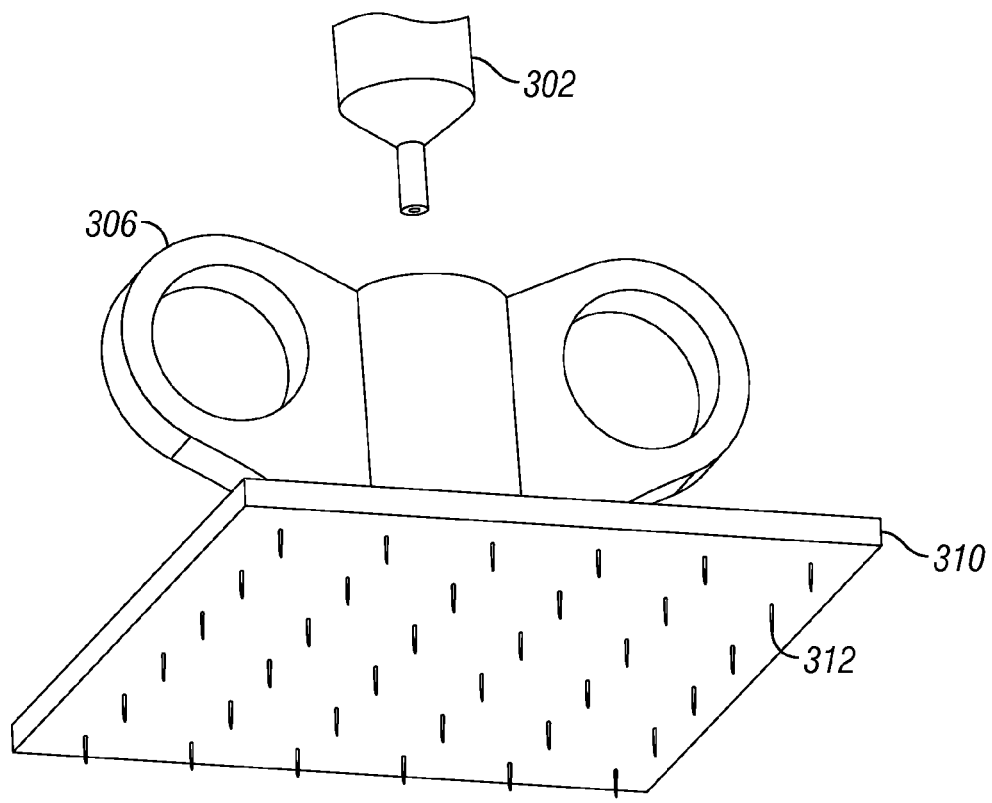

FIGS. 6(a)-(c) depict alternative embodiments of a drug delivery device 300, where a flat array of fine needles 312 of uniform length positioned on manifold 310 can be utilized for drug delivery. In the examples of FIG. 6(a), syringe 302 in which drug for injection is contained can be plugged into a disposable adaptor 306 with handles, and a seal 308 can be utilized to ensure that the syringe 302 and the disposable adaptor 306 are securely coupled to each other. When the syringe plunger 304 is pushed, drug contained in syringe 302 is delivered from syringe 302 into the disposable adaptor 306. The drug is further delivered into the patient's skin through the flat array of fine needles 312 at a uniform depth when the array of needles 312 is pushed into a patient's skin until manifold 310 hits the skin. FIGS. 6(b)-(c) depict top and bottom views of the drug delivery device 300 with a flat array of fine needles 312, respectively.

The use of the drug delivery device 200 may have as many clinical applications as the number of pharmacological agents that require transcutaneous injection or absorption. For non-limiting examples, a few of the potential applications are the injection of local anesthetics, the injection of neuromodulators such as Botulinum toxin (Botox), the injection of insulin and the injection of replacement estrogens and corticosteroids.

In some embodiments, the syringe plunger 210 of the drug delivery device 200 can be powered by, for a non-limiting example, an electric motor. In some embodiments, a fluid pump (not shown) attached to an IV bag and tubing can be connected to the injection chamber 214 and/or the reservoir 208 for continuous injection. In some embodiments, the volume of the syringe plunger 210 in the drug delivery device 200 is calibrated and programmable.

The foregoing description of various embodiments of the invention has been presented for purposes of illustration and description. Various methods of the invention are applicable to variety of medical, dermatological and surgical methods including reconstructive and plastic surgery procedures and minimally invasive procedures. It is not intended to limit the invention to the precise forms disclosed. Many modifications, variations and different combinations of embodiments will be apparent to practitioners skilled in this art. Further, elements from one embodiment can be readily recombined with one or more elements from other embodiments.

What is claimed is:

1. An apparatus for treating skin tissue, comprising:
   a drum;
   a drum axel assembly rotatably coupled to the drum, wherein the drum rotates on the drum axel assembly;
   a sleeve removeably coupled to the drum, wherein the sleeve comprises an array of scalpets, wherein the array of scalpets create an array of incisions of skin when the drum is applied to a target tissue site of the skin; and
   a drum harvester comprising an internal area of the drum, wherein the drum harvester is configured to collect skin plugs resulting from transection of the array of incisions of skin.

2. The apparatus of claim 1, wherein the drum is one of circular, semicircular, elliptical, square, flat, and rectangular in shape.

3. The apparatus of claim 1, wherein each incision of the array of incisions of skin is one of circular, semicircular, elliptical, and square-shaped.

4. The apparatus of claim 1, wherein a length of scalpets of the array of the scalpets varies according to thickness of the target tissue.

5. The apparatus of claim 1, further comprising: an oscillating flat array of scalpets and blade powered or deployed manually, wherein the array is metered to provide a uniform transection.

6. The apparatus of claim 1, comprising a blade that transects the base of the incisions of skin created by the array of scalpets.

7. The apparatus of claim 6, wherein: the blade is a fenestrated blade layer aligned to the array of scalpets.

8. The apparatus of claim 6, wherein: the blade is placed internal to the drum and is connected to the drum axel assembly where the base of the incisions of skin is transected.

9. The apparatus of claim 6, wherein: the blade is placed internal to the drum and is not connected to the drum axel assembly where the base of the incisions of skin is transected.

10. The apparatus of claim 6, wherein the blade is coupled to the drum axel assembly, wherein activation of the blade transects the incisions of skin to form skin plugs.

11. The apparatus of claim 1, wherein percentage of harvest of the tissue site of the donor is determined in part by induction of a normal dermal histology at a skin defect site of a recipient.

12. The apparatus of claim 1, wherein the drum includes an adherent membrane at least one in the internal area of the drum and coupled to the sleeve, wherein the adherent membrane extracts the skin plugs.

13. The apparatus of claim 12, wherein the sleeve comprises the adherent membrane, the array of scalpets, and the blade.

14. The apparatus of claim 12, wherein the adherent membrane is semi-porous.

15. The apparatus of claim 14, wherein the adherent membrane includes an elastic recoil property.

16. The apparatus of claim 14, wherein the adherent membrane is expandable to cover a surface area of the skin.

17. The apparatus of claim 1, further comprising: an irradiated cadaver dermal matrix onto which the transected incisions of skin is placed, wherein a graft of full thickness skin is cultured and created onto the dermal matrix for the recipient that is immunologically identical to the donor.

18. The apparatus of claim 17, wherein: the cadaver dermal matrix is cylindrical transected similar in size to the harvested incisions of skin to provide histological alignment of the incisions of skin into the cadaver dermal matrix.

19. A method for treating skin tissue, comprising:
   removeably coupling a sleeve to a drum, wherein the sleeve comprises an array of scalpets, wherein the drum is rotatably coupled to a drum axel assembly, and an internal area of the drum includes a drum harvester;
   rotating the drum on the drum axel assembly and applying the rotating drum to a target tissue site of a skin surface;
   generating an array of incisions of skin at the target tissue site via the array of scalpets, wherein the array of incisions corresponds to the array of scalpets, wherein skin plugs resulting from transection of the array of incisions of skin are collected in the drum harvester.

20. The method of claim 19, comprising evoking at least one of cellular and extracellular responses via the array of incisions.

21. The method of claim 19, further comprising: transecting a variable portion of any soft tissue structure without resorting to a standard surgical resection.

22. The method of claim 19, further comprising: performing pixilated mucosal reduction to reduce the significant morbidity associated with more standard surgical procedures for the treatment of sleep apnea and snoring.

23. The method of claim 19, further comprising: performing pixilated skin and vaginal mucosal resection to reestablish normal pre-partum geometry and function without resorting to a vaginal resections for birth injuries of the vaginal vault.

24. The method of claim 19, further comprising: transecting the base of the incisions of skin created by the array of scalpets via a blade, wherein the blade is placed internal to the drum and is connected to the drum axel assembly.

25. The method of claim 19, further comprising: transecting the base of the incisions of skin created by the array of scalpets via a blade, wherein the blade is placed internal to the drum and is not connected to the drum axel assembly.

26. The method of claim 19, comprising transecting incisions of the array of incisions by activating a blade, wherein the transecting forms skin plugs, wherein the blade is coupled to the drum axel assembly.

27. The method of claim 19, further comprising: transecting the base of the incisions of skin created by the array of scalpets via a blade, wherein the blade is placed external to the drum and is not connected to the drum axel assembly.

28. The method of claim 19, further comprising: performing a skin grafting operation by harvesting the transected incisions of skin from a tissue site of a donor onto a skin defect site of a recipient with reduced scarring of the patient's donor site via a drum harvester placed inside the drum.

29. The method of claim 19, further comprising: determining percentage of harvest of the tissue site of the donor in part by induction of a normal dermal histology at the skin defect site of the recipient.

30. The method of claim 19, further comprising: extracting and aligning the transected incisions of skin onto an adherent membrane lined in the interior of the drum.

31. The method of claim 19, further comprising: placing the transected incisions onto an irradiated cadaver dermal matrix of skin; culturing and creating a graft of full thickness skin on the dermal matrix for the recipient that is immunologically identical to the donor.

* * * * *